(12) United States Patent
Armato et al.

(10) Patent No.: US 7,285,637 B2
(45) Date of Patent: Oct. 23, 2007

(54) METHOD FOR THE PREPARATION OF A NON-WOVEN SILK FIBROIN FABRICS

(75) Inventors: Ubaldo Armato, Caldogno (IT); Ilaria Dal Pra, Caldogno (IT); Claudio Migliaresi, Trento (IT); Antonella Motta, Milan (IT); Kemal Kesenci, Dortyol-Hatay (TR)

(73) Assignee: Consorzio per GLI Studi Universitari, Verona (IT)

( * ) Notice: Subject to any disclaimer, the term of this patent is extended or adjusted under 35 U.S.C. 154(b) by 500 days.

(21) Appl. No.: 10/398,252

(22) PCT Filed: Sep. 28, 2001

(86) PCT No.: PCT/IT01/00501

§ 371 (c)(1),
(2), (4) Date: Apr. 2, 2003

(87) PCT Pub. No.: WO02/29141

PCT Pub. Date: Apr. 11, 2002

(65) Prior Publication Data

US 2004/0097709 A1    May 20, 2004

(30) Foreign Application Priority Data

Oct. 2, 2000   (IT) .............................. VR00A0096

(51) Int. Cl.
*D01F 4/02* (2006.01)
*C07K 14/00* (2006.01)

(52) U.S. Cl. ........................ 530/353; 530/355; 514/12; 435/7.1

(58) Field of Classification Search ................ 530/353, 530/355; 514/12; 435/7.1
See application file for complete search history.

(56) References Cited

U.S. PATENT DOCUMENTS

| 976,977 A | 11/1910 | Baumann et al. |
| 5,171,505 A * | 12/1992 | Lock .......................... 264/202 |

FOREIGN PATENT DOCUMENTS

| DE | 198 41 649 | 4/2000 |
| EP | 0 488 687 | 6/1992 |

OTHER PUBLICATIONS

Raje et al., Man-Made Textiles in India 41(4), 160-167 (1998).*
N. Minoura, M. Tsukada, M. Nagura, "Physico-chemical properties of silk fibroin membrane as a biomaterial" Biomaterials,11, pp. 430-434, 1990 (On Order).
M. Demura, T.Asakura, T. Kuroo, "Immobilization of biocatalyst with Bombix mori silk fibroin by several kinds of physical treatment and its application to glucose sensors", Biosensors, pp. 361-372, 1989 (On Order).
T. Hanawa, A. Wanabe, T. Tsuchiya, R. Ikoma, M. Hidika, M. Sugihara, "New oral dosage form for elderly patients: Preparation and characterization of silk fibroin gel", Chem. Pharm. Bull. 43, 284-288, 1995 (On Order).

* cited by examiner

*Primary Examiner*—Chih-Min Kam
(74) *Attorney, Agent, or Firm*—Greenberg Traurig, LLP (57) ABSTRACT

A process for producing non-woven silk fiber fabrics comprises the following steps: a) obtaining silk fibroin, for example either from silk cocoons, or silk textiles or waste silk; b) removing the sercin layer covering the silk fibroin fibers, when present; c) breaking the disulfide bonds between heavy (350 kDa) and light (27 kDa) chains of silk fibroin in order to obtain the production of chain fragments which serve as a specific cellular recognition sites promoting the attachment and growth of cells, d) homogenising of the material resulting from step c).

14 Claims, 6 Drawing Sheets

METHOD FOR THE PREPARATION OF A NON-WOVEN SILK FIBROIN FABRICS

This application is a 371 of PCT/IT01/00501, filed Sep. 28, 2001, which claims the foreign priority of Italy VR2000A000096, filed Oct. 2, 2000.

TECHNICAL FIELD

The present invention relates to a method for the preparation of silk fibroin non-woven fabrics. More specifically, the present invention refers to a method for the preparation of silk fibroin non-woven fabrics forming structures suitable to be used as implant biomaterials, cell culture scaffolds for tissue engineering applications, cell carriers and even biological fluid-filtering systems and protein adsorption.

BACKGROUND ART

The theory underlying tissue engineering applications essentially consists in combining a natural or synthetic matrix with cells from specific tissue source, in such a way that said cells may be grown in a laboratory and then transplanted into a human body.

Moreover, by using implant materials able to positively interact with cells, specific tissue regeneration processes can be initiated and the de novo formation of whole tissue structures achieved. In many instances, such regenerated tissues will be capable of performing their normal functions eventually lost because of previously suffered damages.

Silk fibroin is a bio-material that can be used in surgery as implant material as well as for tissue engineering applications. In this context it is proper to remark that silk fibroin has very good properties such high strength coupled with flexibility, blood compatibility, water permeability and permeability to oxygen; all this makes silk fibroin an excellent candidate for biomedical applications as either in the form of non-woven membranes and fibers or in the form of woven membranes and fibers.

Silk fibroin makes up 75% to 80% by weight of the raw silk. The silk content of the protein sericin, which surrounds the two kinds of fibroin filaments, varies from 20% to 25% by weight depending on the species, origin, and culture conditions of the raw silk.

Silk fibroin is a fibrous protein whose hierarchical structure consists of fibrils and micro-fibrils, in which the fibers are arranged in a highly oriented crystalline form.

Silk fibroin easily dissolves in a saturated aqueous solution of inorganic salts.

By desalting such a solution by dialysis, an aqueous solution of silk fibroin could be obtained.

Due to the alfa-elix structure of fibroin, these solutions are not stable, and the structure of the regenerated membrane that is obtained from these solutions can be easily changed by polar solvents, ageing, and physical forces (shear, vibration, mixing etc.).

In order to obtain silk fibroin, it is possible to use silk in the form of cocoons, silk textiles and waste silk.

The raw silk filament is not soluble in formic acid due to the presence of an external sericin layer.

In order to eliminate the sericin layer, silk must be first degummed.

With the term "degumming", the partial or complete removal of the sericin that covers the two types of fibroin filaments is intended.

The degumming agents commonly used are mainly alkali-free soaps.

According to a degumming method known in the art, silk is treated in a soap bath at 95-98° C. for a period of 2-4 hours, depending on the quality and type of the fabric.

The use of silk fibroin as a cell culture matrix is already known (see for example the Italian Patent Application No. VR99A000082), as a burn wound dressing membrane (N. Minoura, M. Tsukada, M. Nagura, "Physico-chemical properties of silk fibroin membrane as a biomaterial" Biomaterials, 11, 430-434, 1990), as an enzyme-immobilization material (M. Demura, T. Asakura, T. Kuroo, "Immobilization of biocatalyst with Bombix mori silk fibroin by several kinds of physical treatment and its application to glucose sensors", Biosensors, 361-372, 1989), and an oral dosage form ù(T. Hanawa, A. Wanabe, T. Tsuchiya, R. Ikoma, M. Hidika, M. Sugihara, "New oral dosage form for elderly patients: Preparation and characterization of silk fibroin gel", Chem. Pharm. Bull. 43, 284-288, 1995).

However, silk fibroin membranes are very brittle and their preparation is difficult and time-consuming.

The use of textile methods would theoretically be possible to weave using merely degummed silk fibroin fibers in order to obtain a flexible fabric.

However, preparing three dimensional structures appears to be remarkably difficult, and the adaptability of a tissue obtained in such a way would not be entirely proper to the different applicative requirements in terms of specifically required mechanical attributes, structure, and even ability to interact with other cells.

DESCRIPTION OF THE INVENTION

The aim of the present invention is to provide a method for the preparation of silk fibroin non-woven fabrics formed by a meshwork of fibroin fibers in order to obtain an high flexible material which preserves unchanged at the same time the demonstrated favorable biological functions of silk fibroin.

This is achieved by the features disclosed in the main claim.

The dependent claims outline particularly advantageous forms of embodiment of the method according to the invention.

Moreover, claims 13 and 14 describe a three-dimensional silk fibroin fabrics.

Furthermore, claims 15 and 16 describe particularly favorable uses of a three-dimensional silk fibroin fabrics.

The process according to the invention comprises the initial degumming of silk fibroin using a treatment based on a $NaHCO_3$ solution or on other methods known in the state of the art as degumming methods and described in the scientific literature.

According to the invention, the degummed silk undergoes then a treatment breaking the disulfide bonds between heavy (350 kDa) and light (27 kDa) chains of silk fibroin.

Such treatment is favourably performed partially dissolving the silk fibroin in a formic acid solution.

Afterwards the resulting solution is homogenized and dried obtaining as a result a non-woven fabric comprising the desired properties.

Finally the fabric is washed several times in order to remove possible residues deriving from the previous treatments and kept in wet conditions until use.

According to a form of embodiment of the invention, the formic acid solution used in the process contains a small amount of a mixture of salts selected from the group comprising calcium chloride, zinc chloride, potassium chloride, lithium bromide, lithium thiocyanate, magnesium chloride, copper nitrate and sodium chloride.

Such added salts can be removed washing with double distilled water.

The non-woven silk fibroin fabrics according to the invention proved to allow the co-culture in vitro of normal adult human keratinocytes and fibroblasts (besides other human cell types), thus making up dermoepidermal equivalents apt for in vivo testing.

Moreover, the process according to the present invention proved the formation of bio-functional fragments that could serve as specific cellular recognition sites promoting the attachment and growth of mammalian and human cells.

ILLUSTRATION OF DRAWINGS

Other features and advantages of the invention will become apparent from the following description of some forms of embodiment of the invention, given as a non-limiting example, with the help of the figures illustrated in the attached drawings, in which.

DESCRIPTION OF SOME FORMS OF EMBODIMENT

As indicated above, to obtain silk fibroin, silk as cocoons, silk textiles and waste silk could be used.

Moreover since the raw silk filament is not soluble in formic acid due to the presence of an external sericin layer, silk must be first degummed, to eliminate the sericin layer.

According to the invention, degummed silk is thus treated with a water-formic acid solution.

In this context, solutions having from 88% to 99% by weight of formic acid could be used, with the 99-weight percent formic acid solutions being preferred.

In accordance with a preferred form of embodiment of the process the silk fibroin is dipped into formic acid at room temperature; nevertheless, the process can be carried out at higher temperatures, for example up to 60° C.

The experiments were carried out under a fume-hood.

According to an advantageous form of embodiment of the present invention the degree of solution of the silk fibroin can be increased in order to obtain highly tightened fabrics.

This is achieved by adding an amount from 0.1 to 10% by weight of a salt mixture selected from the group comprising calcium chloride, zinc chloride, potassium chloride, lithium bromide, lithium thiocyanate, magnesium chloride, copper nitrate and sodium chloride.

Preferably the salts to be used are calcium chloride and lithium bromide.

According to the invention, silk fibroin concentrations comprised between 0.1% and 10% by weight have been favourably used. The best result are obtained with concentrations between 0.5% to 5% by weight.

Figure 1A:
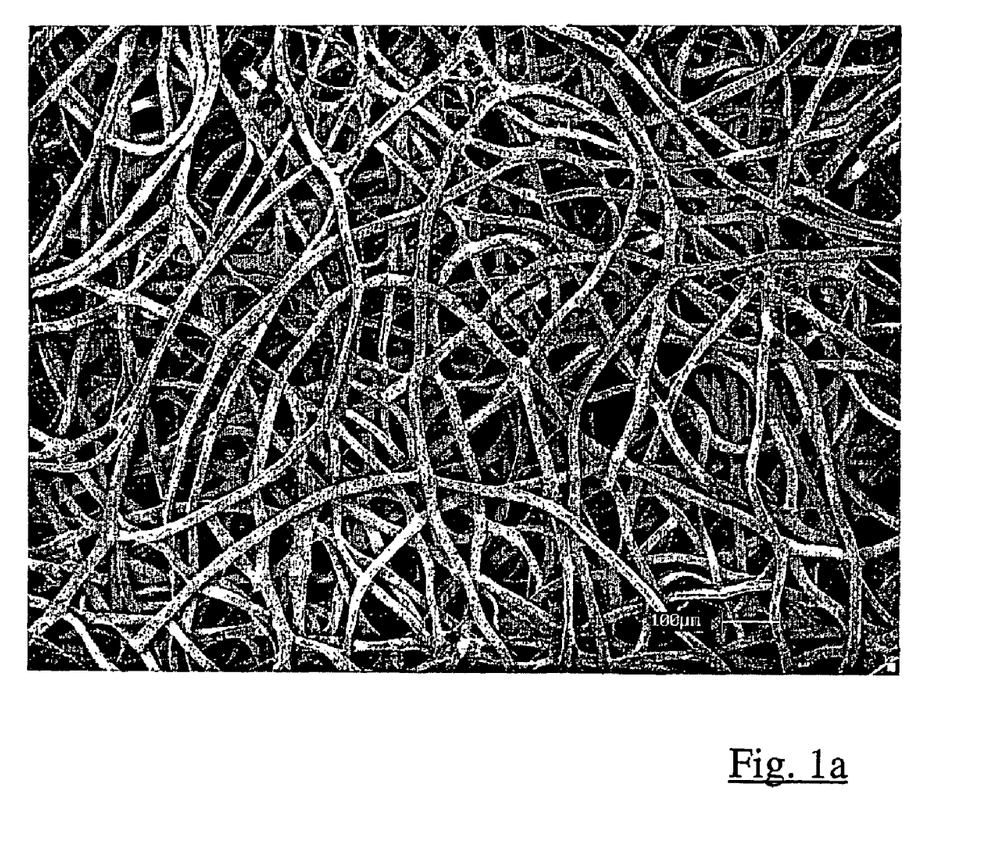
FIGS. 1a and 1b represent scanning electron microscopy (SEM) pictures of silk fibroin fabrics made up by non-woven meshwork of fibers and fibrils bonded together. The picture of FIG. 1a is obtained with a 100 µm scale, while the picture of FIG. 1b is obtained with a 10 µm scale.
Figure 1B:
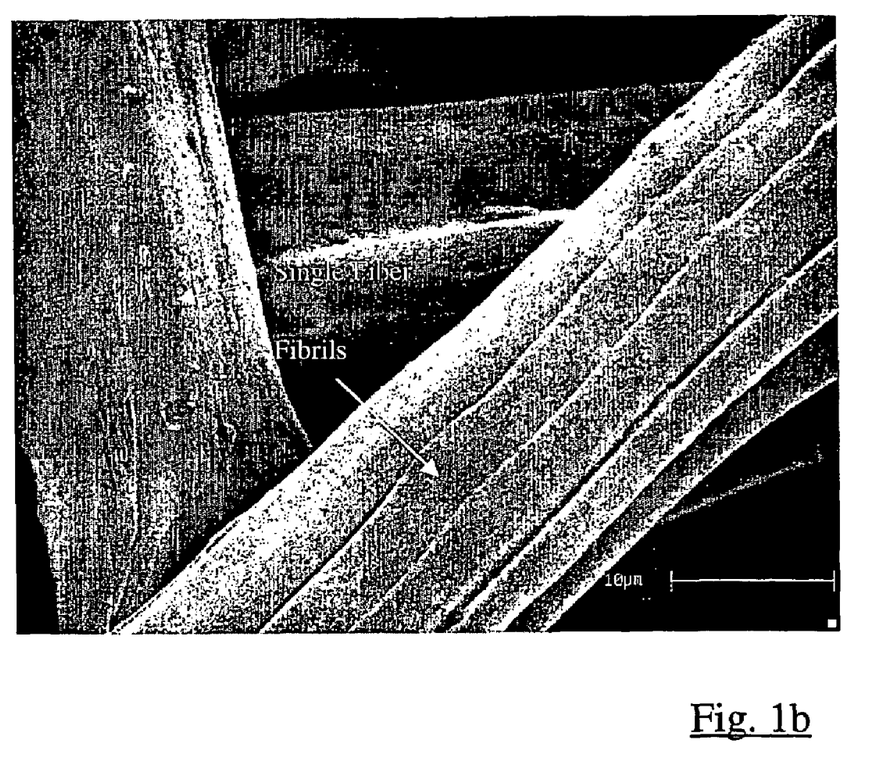

With reference to FIGS. 1a and 1b, the structural hierarchy of silk fibroin fibers consists of fibrils, micro-fibrils and polymer molecules.

Now, according to the present invention, the break of disulfide bonds between heavy (350 kDa) and light (27 kDa) chains of silk fibroin allows the production of chain fragments which can serve as a specific cellular recognition sites promoting the attachment and growth of cells.

Characterization of the silk fibroin fabrics has been performed by using Scanning Electron Microscopy (SEM), Thermogravimetric Analysis (TGA) and Differential Scanning Calorimetry (DSC) and moreover by means of mechanical tests.

EXAMPLE 1

In the following example 0.5 g of degummed silk fibroin (from cocoon, textiles or waste silk) was brought into 100 ml of a water solution of formic acid.

The resulting solution was poured onto clean glass or polystyrene dishes and then stirred at 100 rpm for 30 minutes in order to obtain homogeneously distributed fibers.

The resulting solution was left under atmospheric conditions in order to remove the formic acid.

Once the formic acid had been removed by evaporation at room temperature, the resulting silk fibroin fabrics were washed several times with double distilled water and next dried inside a vacuum oven at 50° C.

In order to increase the solubility of the silk fibroin, calcium chloride was used.

Table 1 as follow reports the characteristics of some of the silk fibroin solutions used.

As can also be seen from the data of Table 1, the process in accordance with the present invention allows the silk fibroin to be dissolved.

TABLE 1

| *Exp. N° | Silk Fibroin (wt %) | CaCl$_2$ (wt %) | Formic acid (ml) | Solubility | Final Resulting Form |
|---|---|---|---|---|---|
| 1 | 0.1 | — | 100 | Partially soluble | Nonwoven fabrics |
| 2 | 0.2 | — | 100 | " | " |
| 3 | 0.3 | — | 100 | " | " |
| 4 | 0.4 | — | 100 | " | " |
| 5 | 0.5 | — | 100 | " | " |
| 6 | 0.6 | — | 100 | " | " |
| 7 | 0.7 | — | 100 | " | " |
| 8 | 0.8 | — | 100 | " | " |
| 9 | 0.8 | — | 100 | " | " |
| 10 | 1.0 | — | 100 | " | " |

TABLE 1-continued

| *Exp. N° | Silk Fibroin (wt %) | CaCl₂ (wt %) | Formic acid (ml) | Solubility | Final Resulting Form |
|---|---|---|---|---|---|
| 11 | 2.0 | — | 100 | " | " |
| 12 | 3.0 | — | 100 | " | " |
| 13 | 4.0 | — | 100 | " | " |
| 14 | 5.0 | — | 100 | Swellable | " |
| 15 | 10 | — | 100 | " | " |
| 16 | 1.0 | 0.5 | 100 | Soluble | Membrane |
| 17 | 2.0 | 1.0 | 100 | " | " |
| 18 | 3.0 | 1.5 | 100 | " | " |
| 19 | 4.0 | 2.0 | 100 | " | " |
| 20 | 5.0 | 2.5 | 100 | " | " |
| 21 | 0.1 | 0.01 | 100 | Soluble | " |
| 22 | 0.2 | 0.01 | 100 | " | " |
| 23 | 0.3 | 0.01 | 100 | Partially soluble | Nonwoven fabrics |
| 24 | 0.4 | 0.01 | 100 | " | " |
| 25 | 0.5 | 0.01 | 100 | " | " |
| 26 | 0.8 | 0.01 | 100 | " | Nonwoven fabrics |
| 27 | 0.8 | 0.1 | 100 | Soluble | Membrane |
| 28 | 0.8 | 0.2 | 100 | " | " |
| 29 | 0.8 | 0.4 | 100 | " | " |
| 30 | 10 | 5 | 100 | " | " |

*All the experiments were performed at room temperature

As can be noted from the data of Table 1, the process according to the present invention caused a homogenous, swellable, partially soluble or soluble mass that is obtained by breaking the disulfide bonds between the heavy (350 kDa) and light (27 kDa) chains of silk fibroin Some characteristic properties of the silk fibroin fabrics produced by means of the process according to the invention are given in Table 2.

TABLE 2

| | Wet State | | | Dry State | | |
|---|---|---|---|---|---|---|
| Sample N°. | Modulus (Mpa) | Elongation (%) | Pore size* (µm) | Modulus (Mpa) | Elongation (%) | Pore size* (µm) |
| 5 | 35 | 43 | 30-200 | 500 | 34 | 50-250 |
| 10 | 60 | 36 | 10-150 | 450 | 25 | 30-200 |
| 15 | 70 | 40 | 10-100 | 700 | 27 | 20-100 |
| 20 | 130 | 56 | — | 3000 | 10 | — |
| 25 | 75 | 55 | 50-250 | 670 | 30 | 50-300 |
| 30 | 120 | 60 | — | 5000 | 7 | — |

*Pore sizes as measured by SEM and optical microscopy

Tensile properties of silk fibroin are usually measured via a load-extension test.

According to the ASTM 638, all test were performed at room temperature in wet and dry states. As it can be seen in Table 2, due to the water, the modulus of meshwork and membranes is increased; besides, elongation is decreased.

Morphology of the silk fibroin fabric has been also checked by SEM and optical and fluorescence microscopy. It can be clearly noted in SEM photographs that voids are distributed randomly and can be controlled by the concentration of silk fibroin or by preparing multiple layers of silk fibroin fiber structures.

Figure 2:
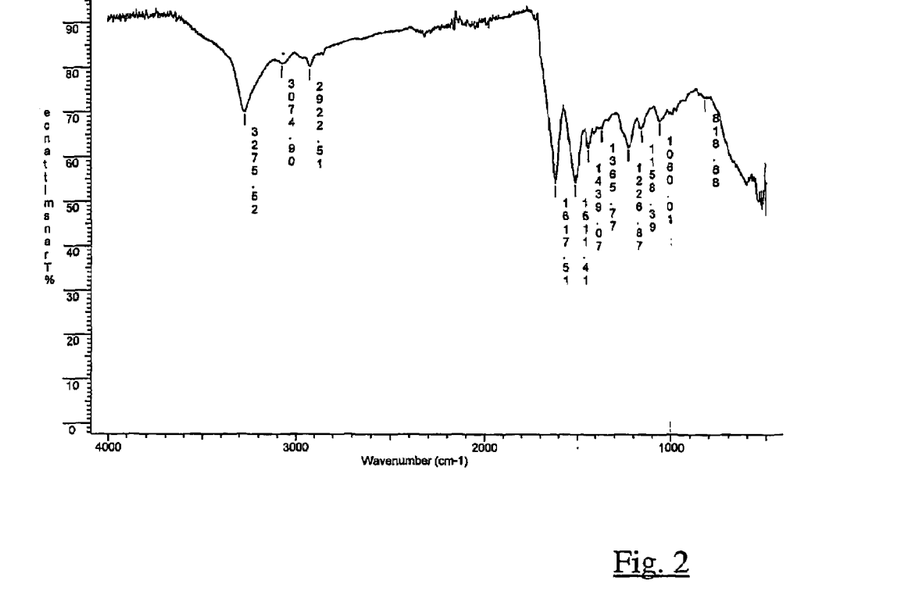
FIG. 2 shows a typical infrared spectrum of formic acid treated silk fibroin.

FIG. 2 shows a typical infrared spectrum of formic acid treated silk fibroin. It can be noted that all compositions exhibited an approximately similar FTIR spectrum; FIG. 2 comprises Amide I, Amide II, Amide III and Amide IV bands respectively.

Figure 3:
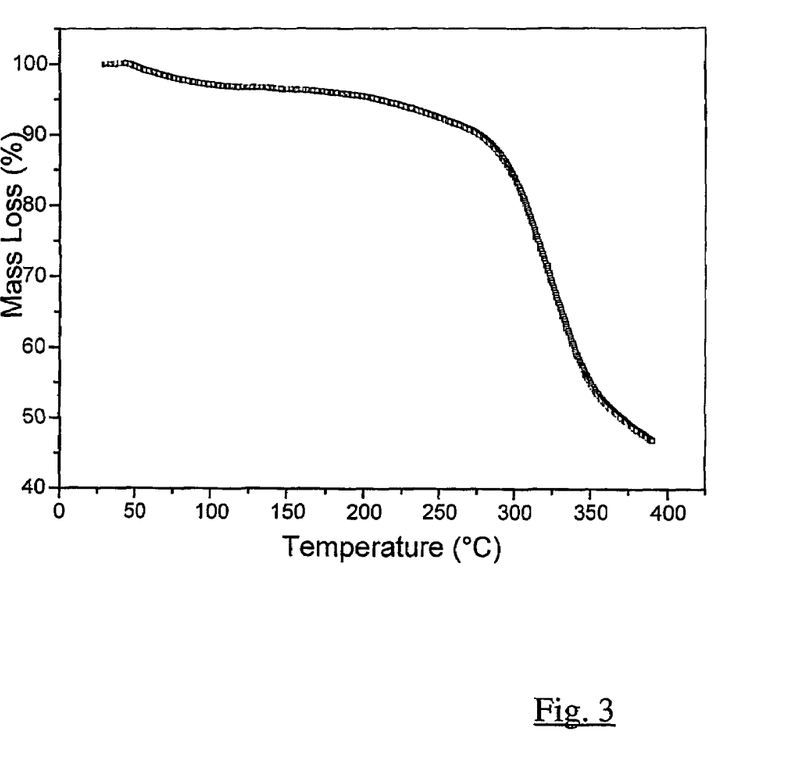
FIG. 3 shows a typical thermal gravimetric analysis of formic acid treated silk fibroin.

FIG. 3 shows a typical thermal gravimetric analysis of formic acid treated silk fibroin; such analysis was performed with the aim to check water absorption and thermal decomposition properties.

In the thermogram shown in FIG. 3, all samples behaved in the same way: the water content of the samples stored under environmental conditions is the range from 5 to 10% by weight, and decomposition starts to temperatures beyond 280° C.

EXAMPLE 2

A three-dimensional fibroin fiber fabric was prepared according to the following method.

A first layer 200 µm thick with a mean pore diameter of 15 µm was coupled to a second layer having 1200 µm thick with a mean pore diameter of 40 µm. The two layers were prepared separately and joined together applying a suitable pressure forming a fabric with a total thickness of 1.5 mm.

The material was sterilized exposing for about 30 minutes each of its two sides to ultraviolet rays emitted by bactericidal lamps contained inside a closed box at room temperature; afterwards it was cut into 2.7×2.9 cm square pieces that were each laid inside the square wells (8.6 square centimetres each) of 8-well Multidish plates (Nunc Ltd.).

Normal human dermal fibroblasts were isolated from an intra-operative biopsy (the patient was informed and consenting) by means of trypsin digestion (trypsin solution 0.25% p/v) of the minced dermal layer and were then numerically expanded in standard TC75 tissue culture flasks (Falcon Ltd.) containing 15 mL of Dulbecco's Minimum Essential Medium (DMEM; Sigma Chemical Co.) fortified with 5% by volume of inactivated (56° C. for 30 min.) foetal bovine serum (Biowhittaker SpA).

Prior to seeding onto the fibroin fabric, fibroblasts were detached from the bottom of the flasks, then labelled with 3,3'-dioctadecyloxacarbocyanine perchlorate, an intra-vital stain emitting a bright green fluorescence visible with an optical FITC filter set when excited by ultraviolet light (Molecular Probes Inc.), and finally counted.

About 100,000 fibroblasts were next seeded onto each square centimetre of the pieces of the just above described fibroin fabric.

Prior to seeding, the fabric pieces had been turned so that their portions endowed with larger pores looked upwards.

The specimens were then incubated at 37° C. in an atmosphere of air added with CO2 (5% volume).

The fibroblasts attached immediately to the fibroin fibers and it was possible to verify a percentage of fibroblasts not attaching to the fibroin fabric less than 1% of the total number of the fibroblasts seeded.

Figure 4:
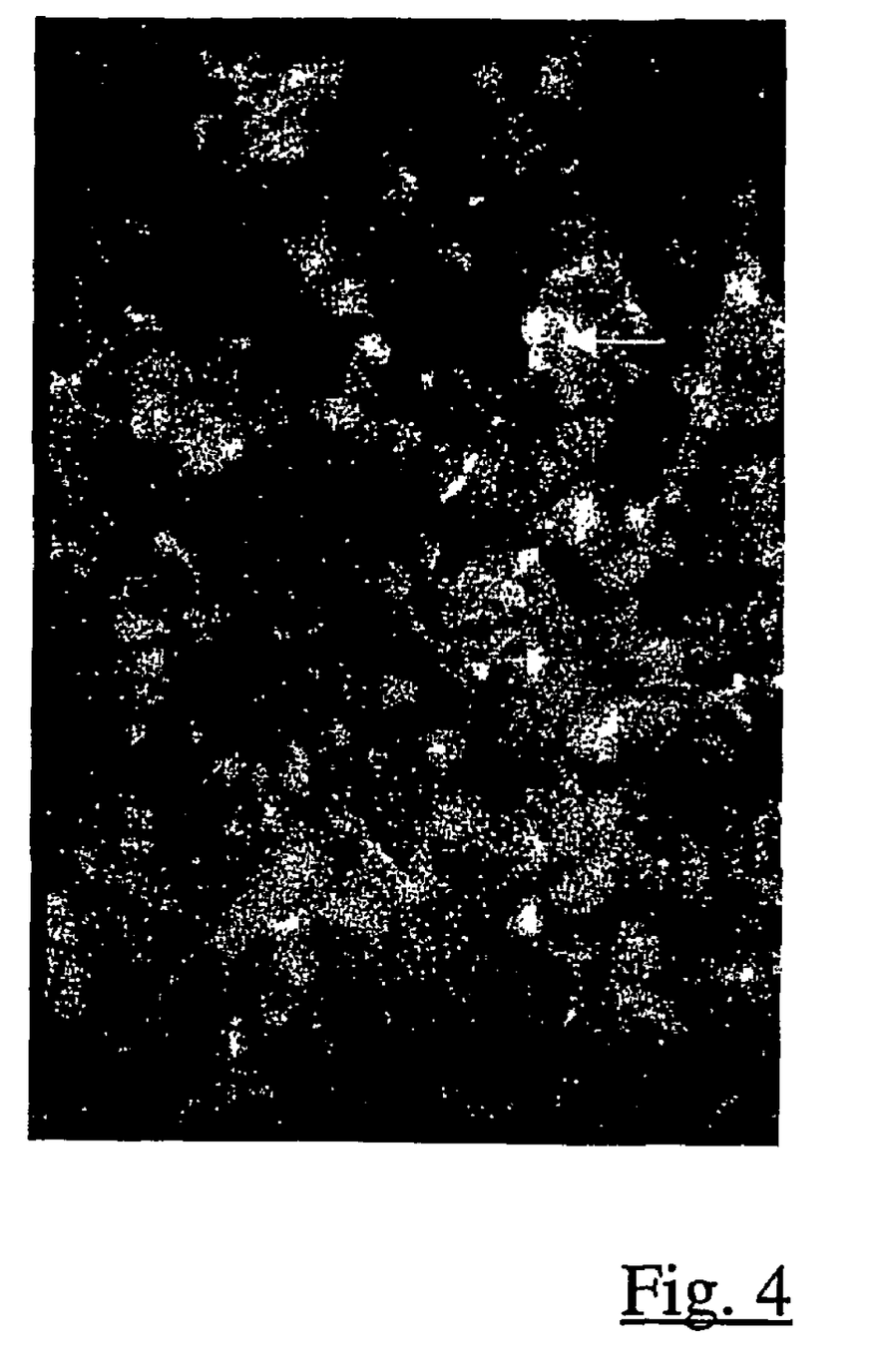
FIG. 4 is a picture made under fluorescence microscopy (fluorescein [FITC] optical filter set) and shows scattered normal adult human fibroblasts cultured in-vitro for 10 days on a fibroin meshwork. Prior to seeding, fibroblasts were labelled with 3,3'-dioctadecyloxacarbocyanine perchlorate: thus, the living cells emit a bright green fluorescence, the intensity of which peaks at about 590 nm wavelength, when excited by ultraviolet light. A weak greenish auto-fluorescence proper for the fibroin fibers can also be appreciated. Original magnification, 100×.

The fibroblasts proliferated intensely, as could be detected under a fluorescence microscopic examination (see FIG. 4).

They were cultured and grew up for 10 consecutive weeks on pieces of fibroin fabric.

Not only their increase in numbers was detectable under the fluorescence microscope, but it was further confirmed by their increasing consumption of the glucose present in the medium.

The vitality and high anabolic metabolism of the cells was confirmed also by the practical absence of urea nitrogen (a measure of protein demolition) from the conditioned growth media.

Normal human epidermal keratinocytes isolated from an intra-operative biopsy (the patient was informed and consenting) by dispase digestion were first seeded onto a layer of previously irradiated human fibroblasts (6000 rads;

feeder-layer) and expanded by exposure to a mixture 1:1 volume of MCDB 153 medium (Sigma) and Ham's F12 medium (Biowhittaker GmbH) added with 5% by volume of inactivated (56° C. for 30 min) foetal bovine serum.

At 70% confluence the keratinocytes were detached from the flasks, then labelled with 1,1'-dioctadecyl-3,3,3,3'-tetramethylindocarbocyanine perchlorate, an intra-vital fluorescent stain emitting an orange-red bright fluorescence under a rhodamine optical filter set when excited by ultraviolet light (Molecular Probes Inc.), and next counted.

About 100,000 keratinocytes were then seeded onto each square centimetre of the same pieces of fibroin fabrics on which human fibroblasts were already attached In this case the tissue pieces were turned in such a way that their portions with smaller pores looked upwards.

The specimens were then incubated at 37° C. in an atmosphere of air added with CO2 (5% by volume).

The keratinocytes attached immediately to the fibroin meshwork of fibers as well and the percentage of the keratinocytes not adhered to the fibroin was irrelevant.

Figure 5:
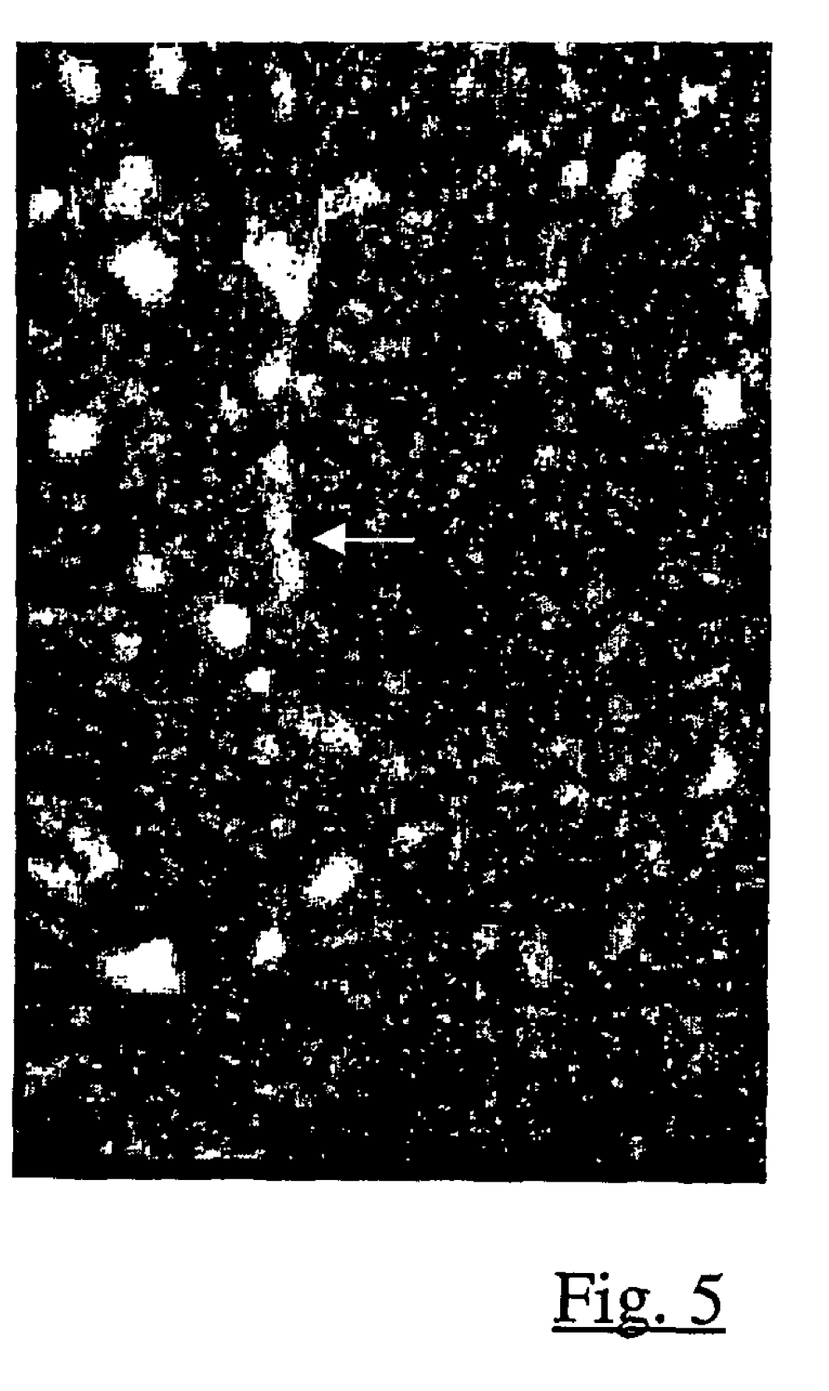
FIG. 5 shows the same specimen as in FIG. 4, but observed under the fluorescence microscope with a rhodamine optical filter set. The examination shows several islets of normal human keratinocytes, co-cultured for 4 days with the fibroblasts on the fibroin meshwork, fluoresce orange red. Prior to seeding, keratinocytes were labelled with 1,1'-dioctadecyl-3,3,3,3'-tetramethylindocarbocyanine perchlorate: thus, they are observed as spots emitting an intra-vital orange red fluorescence, peaking at about 500 nm wavelength, when excited by ultraviolet light. Original magnification, 100×.

As expected, the keratinocytes grew slowly at the beginning, but after 3-4 days their growth became faster, therefore large patches of cells were formed that were easily detectable under the microscope for their intense red fluorescence and perfectly distinguishable from the co-cultured fibroblasts fluorescing in green with optical FITC filters and located in the lower layer of the fibroin meshwork (see FIG. 5.)

Thus, the above description evidences that the fibroin fiber fabric according to the invention allows the in vitro production of an entirely new type of a dermal-epidermal equivalent which may be used in vivo as an artificial skin.

The invention described above refers to some of its particular forms of embodiment.

However, it is clear that the invention encompasses all the modifications and variations that can be considered, without going beyond the framework of the present invention as claimed.

As an example, it is clear that, on the base of the model disclosed above, other three-dimensional non-woven fibroin fabrics can be endowed with ad hoc attributes and thus to be used as scaffolds for the engineering of other tissues (such as arteries, tendons, cartilage, bone, etc) or organs (trachea, oesophagus, liver, etc.) to be grafted or connected to the organism temporarily (e.g. bio-artificial liver systems) or permanently in vivo.

The invention claimed is:

1. A method for producing non-woven silk fiber fabrics comprising the following steps:
   a) preparing silk fibroin solution by adding degummed silk fibroin to formic acid solution having a concentration of formic acid from 88% to 99% by weight;
   b) mixing the solution to facilitate breaking of the disulfide bonds between heavy (350 kDa) and light (27 kDa) chains of silk fibroin in order to obtain the production of light and heavy chain fragments, wherein said chain fragments serve as a specific cellular recognition sites for promoting the attachment and growth of cells;
   c) removing the formic acid to obtain non-woven silk fiber fabrics; and
   d) washing the obtained non-woven silk fiber fabrics.

2. The method according to claim 1, wherein said degummed silk fibroin is obtained by using a treatment based on a $NaHCO_3$ solution.

3. The method according to claim 1, in which said formic acid solution is a formic acid water solution.

4. The method according to claim 3, in which said silk fibroin concentrations in said solution are in a range between 0.1% and 10% by weight.

5. The method according to claim 1, wherein said step a) and/or step b) is carried out at temperatures not higher than 60° C.

6. The method according to claim 5, wherein said step a) and/or step b) is carried out at room temperature.

7. The method according to claim 1, wherein the solution contains 0.1% to 10% by weight of a mixture of salts selected from the group consisting of calcium chloride, zinc chloride, potassium chloride, lithium bromide, lithium thiocyanate, magnesium chloride, copper nitrate and sodium chloride.

8. The method according to claim 1, wherein the solution contains 0.1% to 5% by weight of calcium chloride.

9. The method according to claim 1, wherein the breaking of the disulfide bonds is obtained by stirring the solution for a predetermined period of time.

10. The method according to claim 1, wherein the formic acid is removed by evaporation.

11. The method according to claim 1, wherein the obtained non-woven silk fiber fabrics is washed several times with double distilled water and then dried.

12. The method according to claim 11, wherein drying of the silk fiber fabrics is carried out in a chamber at a predetermined and controlled temperature.

13. A method of utilizing a non-woven silk fiber fabrics in tissue engineering comprising:
   a) preparing silk fibroin solution by adding degummed silk fibroin to formic acid solution having a concentration of formic acid from 88% to 99% by weight;
   b) mixing the solution to facilitate breaking of the disulfide bonds between heavy (350 kDa) and light (27 kDa) chains of silk fibroin in order to obtain the production of light and heavy chain fragments, wherein said chain fragments serve as a specific cellular recognition sites for promoting the attachment and growth of cells;
   c) removing the formic acid to obtain non-woven silk fiber fabrics;
   d) washing the obtained non-woven silk fiber fabrics; and
   e) utilizing the silk fiber fabrics as scaffolds in tissue engineering, wherein the scaffolds are suitable to prepare in vitro cultures of isolated cells or cells-forming tissues.

14. The method according to claim 13, wherein the tissues prepared are skin, vessels, tendons, cartilage, or bone.

* * * * *